United States Patent
Mottola et al.

(10) Patent No.: US 7,766,898 B2
(45) Date of Patent: Aug. 3, 2010

(54) NON-CIRCULAR SIDE PORT BORE FOR INTRODUCER SHEATH

(75) Inventors: Jim Mottola, South Jordan, UT (US); Brian Stevens, Pleasant Grove, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 911 days.

(21) Appl. No.: 10/852,351

(22) Filed: May 24, 2004

(65) Prior Publication Data

US 2005/0261630 A1    Nov. 24, 2005

(51) Int. Cl.
*A61M 39/02* (2006.01)
(52) U.S. Cl. .............. 604/539; 604/523; 604/533
(58) Field of Classification Search ............. 604/43, 604/93.01, 164.01, 164.02, 164.04, 164.07, 604/164.08, 164.09, 164.11, 164.13, 166.01, 604/167.01, 523, 539, 264, 533, 534, 538
See application file for complete search history.

(56) References Cited

U.S. PATENT DOCUMENTS

| | | | | |
|---|---|---|---|---|
| 4,000,739 A | * | 1/1977 | Stevens | 604/537 |
| 4,405,314 A | | 9/1983 | Cope | 604/51 |
| 4,682,981 A | * | 7/1987 | Suzuki et al. | 604/158 |
| 4,705,511 A | * | 11/1987 | Kocak | 604/524 |
| 5,000,745 A | * | 3/1991 | Guest et al. | 604/256 |
| 5,334,154 A | | 8/1994 | Samson et al. | 604/102 |
| 5,800,408 A | * | 9/1998 | Strauss et al. | 604/264 |
| 5,817,074 A | | 10/1998 | Racz | 604/272 |
| 6,007,557 A | * | 12/1999 | Ambrisco et al. | 606/200 |
| 6,221,065 B1 | * | 4/2001 | Davis | 604/539 |
| 6,309,382 B1 | * | 10/2001 | Garrison et al. | 606/1 |
| 2003/0100849 A1 | * | 5/2003 | Jang | 600/585 |

* cited by examiner

*Primary Examiner*—Kevin C Sirmons
*Assistant Examiner*—Laura C Schell
(74) *Attorney, Agent, or Firm*—Stoel Rives LLP (57) ABSTRACT

The present invention is directed towards a side port for an introducer sheath which precludes the inadvertent excursion a guide wire (or other article or material) through a side port while advancing through the main lumen of an introducer sheath. To prevent inadvertent excursions of a guide wire, the introducer sheath has one or more non-circular side ports. The non-circular component of the side port has a minimum transverse dimension that is smaller than the diameter of the guide wire to be introduced through the lumen of the introducer sheath. Therefore, the small diameter of the non-circular component of the side port prevents a guide wire from inadvertently entering the side port.

30 Claims, 8 Drawing Sheets

NON-CIRCULAR SIDE PORT BORE FOR INTRODUCER SHEATH

BACKGROUND OF THE INVENTION

1. The Field of the Invention

The present invention relates generally to introducer sheaths. In more particular, the present invention relates to an introducer sheath with one or more side ports having non-circular lumens utilized in the delivery of one, or a combination of, saline, medicines, or other materials or fluids.

2. The Relevant Technology

Introducer sheaths are typically used in surgical and clinical procedures allowing access to and bloodless exchange of guide wires, catheters, contrast media, and various fluids including medications and bodily fluids. Introducer sheaths are inserted percutaneously and/or intravenously into the patient to provide a connection point between the patient and the introduced matter. Introducer sheaths are capable of delivering matter without requiring a new puncture site for each article or material to be introduced. By reducing repeated percutaneous punctures and providing a single delivery apparatus for items to be introduced intraveneously, introducer sheaths help protect the patient from unnecessary punctures and thereby reduce pain and trauma to the patient. As refereed to above, introducer sheaths are also used for extracting matter (ie., bodily fluids, samples, etc) from the patient.

Introducer sheaths typically include a side port having an internal bore or lumen that is in fluid communication with the main lumen of the introducer sheath. Side ports of introducer sheaths are utilized to allow the introduction and/or removal of materials and objects into and out of the patient. For example, a side port can be configured to be configured to be coupled to a saline and/or medicinal bag. The side port can be used to deliver medicines intraveneously to the patient without obstructing the main lumen of the introducer sheath. Alternatively, the side port can be used to withdraw blood or fluids for analysis during a procedure. This allows the practitioner to conduct procedures with a guidewire, stent, balloon, catheter, or other article without needing to disconnect and/or extract tubing or discontinue delivery of medicines before the guidewire or other article is introduced.

One problem encountered in the use of a side port with an introducer sheath relates to threading of catheters through the main lumen of the introducer sheath. One type of guide wire that is used in angioplasty and other procedures utilizes a curved portion on the advancing end that resembles a "J". As "j type" guide wires move from the distal opening of the introducer sheath through the main lumen of the introducer sheath, the "j type" tip of the guide wire can engage the lumen/internal bore of the side port. Upon engaging the lumen/internal bore of the side port, further progression of the guide wire can occur into the side port rather than into the patient. This can result in delays as the procedure is being performed while the practitioner remedies the problem.

To prevent movement of the guide wire from the main lumen of the introducer sheath into the lumen/internal bore of the side port, some medical equipment manufacturers have reduced the diameter of the internal bore of the side port. The diameter of the lumen/internal bore is made smaller than the diameter of the guide wire to prevent movement, or excursions, of the guide wire into the lumen/internal bore of the side port. However, the smaller diameter of the lumen/internal bore also reduces the amount of fluid flow through the side port. The amount of fluid flow can be an important feature of the side port particularly where large amounts of fluid or highly viscous fluids are to be introduced through the side port.

BRIEF SUMMARY OF THE INVENTION

The present invention is directed towards a side port for an introducer sheath which minimizes the inadvertent excursion of a guide wire or other article or material from the main lumen of an introducer sheath into the lumen/internal bore of the side port while also providing a larger cross-section of the lumen/internal bore to allow needed articles or materials to be effectively introduced from the side port.

To prevent inadvertent movement of a guide wire from the main lumen of the introducer sheath into the lumen/internal bore of the side port, the introducer sheath has one or more non-circular side ports. The side port lumen/internal bore has a non-circular cross-section of a minimum transverse dimension that is smaller than the diameter of the guide wire to be introduced through the lumen of the introducer sheath. While the non-circular aspect of the side port has a sufficiently small transverse dimension to minimize movement of a guide wire into the lumen/side port, the overall cross-sectional area allows articles or materials to be introduced from the side port into the main lumen of the introducer sheath.

These and other objects and features of the present invention will become more fully apparent from the following description and appended claims, or can be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PRESENT INVENTION

Introducer sheaths are typically used in surgical and clinical procedures requiring the introduction of guide wires, catheters, stents, and other articles and materials into a patient's vasculature. Introducer sheaths allow access to the patient's vasculature while allowing the bloodless exchange of a series of guide wires, catheters, stents, balloons, contrast media, fluids (such as medications or bodily fluids), and other articles or materials.

A portion of an introducer sheaths is inserted percutaneously and/or intraveneously into the patient to provide a connection point between the patient and the articles and/or matter to be introduced. Introducer sheaths are capable of delivering the introduced articles without requiring a new puncture site for each article or material to be introduced. By reducing repeated percutaneous punctures and providing a single delivery apparatus for all matter and materials to be introduced, the introducer sheath helps protect the patient from unnecessary punctures and thereby reduce pain and trauma to the patient. Introducer sheaths can also be used to extract matter (ie., bodily fluids, clots, samples, etc) from the patient.

According to one embodiment of the present invention, the introducer sheath includes one or more non-circular side ports lumens/ internal bores that provide an additional opening for the introduction of guide wires, catheters, medicines, and other articles or materials. While the non-circular aspect of the side port can apply to a side port lumen, side port internal bore, or any other internal opening of the side port, without limiting the scope and spirit of the present invention and for the sake of clarity and to simplify the description of the present invention, the non-circular aspect of the side port will be described as a non-circular side port or a non-circular internal bore.

The opening also allows for the extraction of matter, such as sampling of blood, fluids, and other matter from the patient. The materials introduced or extracted utilize the side port and the main lumen of the introducer sheath to communicate materials to/from the patient. By utilizing a non-circular cross-section, the minimum transverse dimension of the introducer sheath can prevent a guide wire from moving into the side port while allowing a greater amount of fluid flow. The greater amount of fluid flow is facilitated by providing a larger cross-sectional area than a circular side port having diameter smaller than the diameter of the guide wire. The larger cross-sectional area allows a greater amount of fluid flow while being sufficiently narrow to stop movement of the guide wire into the side port. The non-circular aspect of the side port can be provided by an internal bore of the side port. The non-circular internal bore has a larger cross-sectional area than a circular side port having the same minimum transverse diameter.

Figure 1:
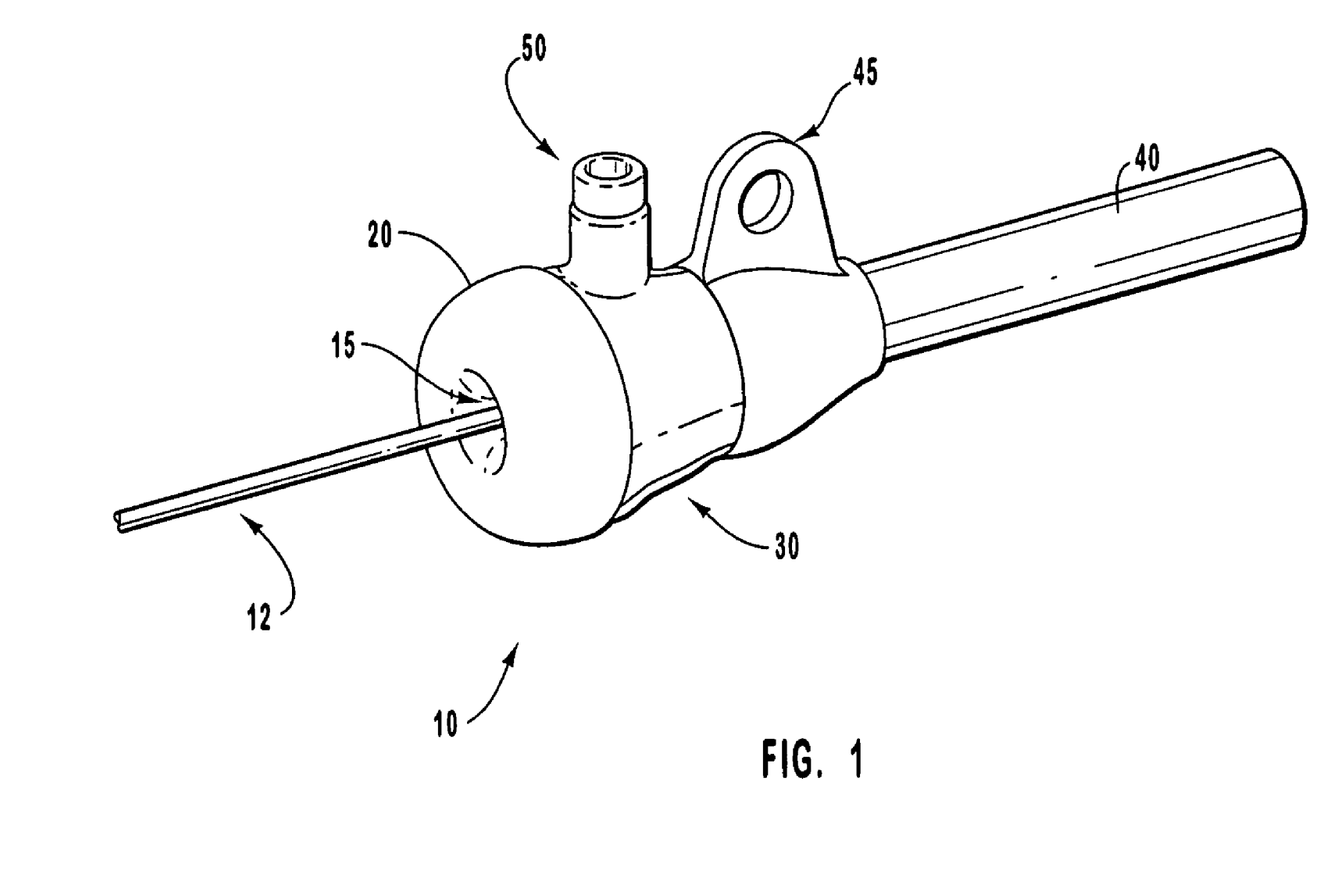
FIG. 1 is a perspective view of the introducer sheath having a side port.

FIG. 1 is a perspective view of introducer sheath 10 illustrating operation of introducer sheath 10 with respect to a guide wire 12. As depicted in FIG. 1, introducer sheath 10 is capable of accommodating materials, such as guide wire 12, that are to be introduced percutaneously and/or vascularly. Guide wire 12 is generally used to facilitate proper threading of a catheter to a desired location within a patient's blood vessel. To accomplish this, guide wire 12 is threaded into introducer sheath 10 so as to thread guide wire 12 intravenously into the patient. Guide wire 12 is then threaded to the desired location within the patient's vasculature. A catheter is then threaded over guide wire 12 until the catheter reaches the desired location.

In the illustrated embodiment, introducer sheath 10 includes an external opening 15, an end cap 20, a seal 25, an introducer sheath body 30, a main lumen 35, a side port 50, and a suture ring 45. End cap 20 accommodates the introduction of guide wire 12 or other articles and materials to be introduced into main lumen 35 of introducer sheath 10. External opening 15 of introducer sheath 10 comprises an aperture defined by proximal end 21 of end cap 20 (see FIG. 2). External opening 15 extends through distal end 22 of end cap 20 (see FIG. 2). Seal 25 is positioned adjacent external opening 15. Seal 25 is configured to prevent leakage of blood and/or fluids as a catheter or other article is introduced into main lumen 35 through external opening 15 of introducer sheath 10.

Introducer sheath body 30 is positioned distally to end cap 20. Introducer sheath body 30 provides support to other components of introducer sheath 10. Introducer sheath body 30 includes a main lumen (not shown). The main lumen accommodates and allows passage of introduced guide wires, catheters, or other articles or materials. Side port 50 is coupled to introducer sheath body 30. Side port 50 allows for the introduction of matter from a secondary position. Side port 50 is configured to accommodate a luer coupler, tubing or other means of delivery for infusate, medicines, etc.

An introducer sheath shaft 40 is coupled at the distal end of the introducer sheath 10. Introducer sheath shaft 40 comprises a passageway for receiving and accommodating materials from main lumen 35 and delivering them into the patient's body. Suture ring 45 is coupled to distal end 33 of sheath body 30 (see FIG. 2). Suture ring 45 provides a mechanism allowing the practitioner to grasp introducer sheath 10 while also allowing introducer sheath to be sutured or fastened to the patient once the introducer sheath 10 has been properly placed.

In the illustrated embodiment, a guide wire 12 is positioned through external opening 15. As guide wire 12 advances through external opening 15, it passes through seal 25 (see FIG. 2), and into the main lumen. From the main lumen, guidewire 12 progresses into introducer sheath shaft 40. Side port 50 allows materials to pass through side port 50 and into the main lumen while guidewire 12 is positioned in the introducer sheath 10 and/or in the patient.

Figure 2:
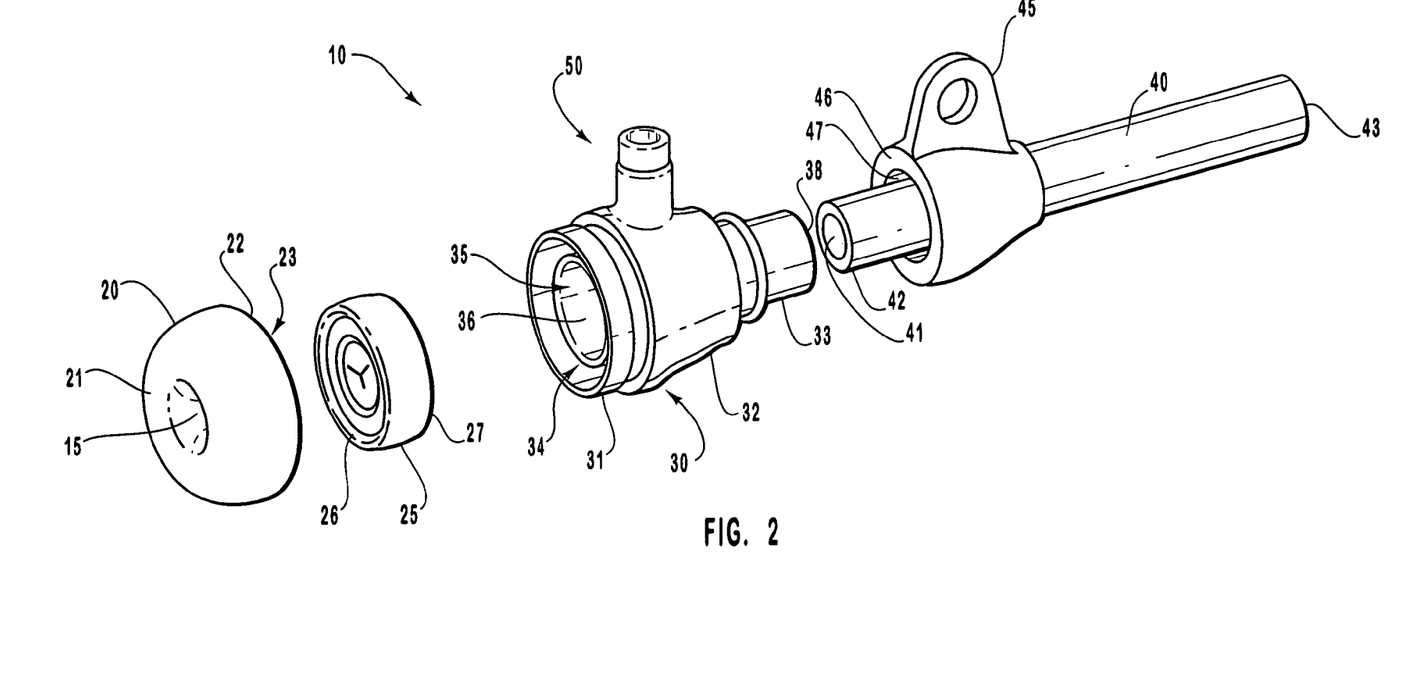
FIG. 2 is an exploded view of an introducer sheath having a side port according to one aspect of the present invention.

FIG. 2 is an exploded view of an introducer sheath 10 according to one aspect of the present invention. As previously discussed, introducer sheath 10 includes external opening 15, end cap 20, seal 25, introducer sheath body 30, main lumen 35, side port 50, and hand grip 45.

External opening 15 of introducer sheath 10 comprises an aperture defined by proximal end 21 of end cap 20. External opening 15 extends through distal end 22 of end cap 20. A seal 25 is positioned adjacent external opening 15. External opening 15 is in fluid communication with main lumen 35 and allows guide wires, catheters, or other articles and/or materials to be introduced into main lumen 35. Seal 25 is configured to minimize leakage of blood from main lumen 35 when such articles or materials are introduced into the main lumen 35 of introducer sheath 10. As will be appreciated by those skilled in the art, a variety of types and configurations of introducer sheaths can be utilized without departing from the scope and spirit of the present invention. For example, in one embodiment, the position and size of the external opening relative to other components of the introducer sheath can vary from that of the illustrated embodiment. In an alternative embodiment, the external opening is non-cylindrical in cross-section.

End cap 20 defines external opening 15 and accommodates the introduction of guide wires, catheters, or other articles or materials to be introduced into main lumen 35 of introducer sheath 10. End cap 20 includes a proximal end 21 and a distal end 22. Proximal end 21 is positioned at the terminal portion of end cap 20. Proximal end 21 defines external opening 15 which extends from distal end 22 into main lumen 35 of introducer sheath 10. Distal end 22 is positioned on the end of end cap 20 opposite proximal end 21. Distal end 22 includes a seal cavity 23 that is capable of enclosing seal 25. Distal end 22 is also configured to attach to distal end 33 of introducer sheath body 30.

Seal 25 is positioned in seal cavity 23. Seal 25 is configured to prevent leakage of blood and other fluids as a catheter or other article is introduced into main lumen 35. In the illustrated embodiment, seal 25 includes a tricuspid slit. Seal 25 includes a proximal portion 26 and a distal portion 27. Proximal portion 26 of seal 25 engages and is partially enclosed within seal cavity 23. Distal portion 27 of seal 25 engages and is enclosed within seal cavity 34 of introducer sheath body 30.

As will be appreciated by those skilled in the art, a variety of types and configurations of seals can be utilized without departing from the scope and spirit of the present invention. For example, in one embodiment, the position and size of the seal relative to the other components of the introducer sheath can vary from that of the illustrated embodiment. In an alternative embodiment, the end cap is non-cylindrical in cross-section. In another embodiment, the valve does not include a tricuspid slit. In yet another embodiment, a valve mechanism configured to prevent leakage of blood or fluids is utilized.

Introducer sheath body 30 is positioned distally to end cap 20. Introducer sheath body 30 provides support to other components of introducer sheath 10. Introducer sheath body 30 includes main lumen 35 that accommodates and allows passage of introduced guide wires, catheters, or other articles or materials. Introducer sheath body 30 includes proximal end 31, intermediate portion 32, and distal end 33.

Proximal end 31 of introducer sheath body 30 receives and accommodates guide wires, catheters or other articles or materials introduced through external opening 15. Proximal end 31 is configured to be attachable to end cap 20. Proximal end 31 includes a seal cavity 34 which partially encloses distal portion 27 of seal 25. Intermediate portion 32 is positioned between proximal end 31 and distal end 33. Intermediate portion 32 includes a side port 50. Side port 50 is configured to be coupled to a saline bag by means of a coupler and tubing to allow the introduction of saline, medicines, and the like into the patient. Side port 50 will be discussed in greater detail with regards to FIGS. 8A-8E. Distal end 33 is positioned on the end of introducer sheath body 30 opposite proximal end 31. Distal end 33 is configured to be attachable to introducer sheath shaft 40 and suture ring 45.

As will be appreciated by those skilled in the art, a variety of types and configurations of introducer sheath bodies can be utilized without departing from the scope and spirit of the present invention. For example, in one embodiment the size of the introducer sheath body relative to the other components of the introducer sheath can vary from that of the illustrated embodiment. In an alternative embodiment, the introducer sheath body is configured to connect to and accommodate multiple side ports. In another embodiment, the introducer sheath body can be integrally coupled to a suture ring and/or a shaft.

Introducer sheath body 30 includes a main lumen 35 that accommodates guide wires, catheters, or other articles and materials. Such articles and materials are introduced into main lumen 35 from external opening 15 and/or side port 50. Main lumen 35 allows passage of such materials into introducer sheath shaft 40. Main lumen 35 includes a proximal portion 36, an intermediate portion (not shown), and a distal portion 38. Proximal portion 36 of main lumen 35 is capable of receiving introduced guide wires, catheters, or other articles and materials from external opening 15. The intermediate section of main lumen 35 is in fluid connection with side port 50. Side port 50 allows additional matter to be introduced into main lumen 35 from a secondary position. Distal portion 38 of main lumen 35 is configured to be in communication with introducer sheath shaft 40 and hand grip 45.

As will be appreciated by those skilled in the art, a variety of types and configurations of the main lumen can be utilized without departing from the scope and spirit of the present invention. For example, in one embodiment the size of the main lumen relative to the other components of the introducer sheath can vary from that of the illustrated embodiment. In an alternative embodiment, the main lumen includes a plurality of side ports. In another alternative embodiment, the main lumen is non-cylindrical in cross-section. In yet another alternative embodiment, the main lumen is integrally coupled to an introducer sheath shaft.

Side port 50 is coupled to introducer sheath body 30. Side port 50 allows for the introduction of matter from a secondary position. Side port 50 is configured to accommodate a luer coupler, tubing or other means of delivery for infusate, medicines, etc. As previously stated, alternative embodiments of the introducer sheath can include multiple side ports that are coupled to the introducer sheath body.

Introducer sheath shaft 40 comprises a passageway for receiving and accommodating materials from main lumen 35 and delivering them into the patient's body. Introducer sheath shaft 40 includes a shaft lumen 41, a proximal end 42 and a distal end 43. Shaft lumen 41 is in fluid communication with main lumen 35 of introducer sheath body 30 so as to receive introduced articles and/or materials and accommodate delivery to the patient.

Proximal end 42 of introducer sheath shaft 40 is attached to introducer sheath body 30 such that shaft lumen 41 is in fluid communication with main lumen 35. Distal portion 43 of introducer sheath shaft 40 is configured to be placed percutaneously and/or intravenuously inside the patient so as to deliver introduced guide wires, catheters, and other articles or materials to a desired location. As will be appreciated by those skilled in the art, a variety of types and configurations of the introducer sheath shaft can be utilized without departing from the scope and spirit of the present invention. For example, in one embodiment the size of the introducer sheath shaft relative to the other components of the introducer sheath can vary from that of the illustrated embodiment. In another alternative embodiment, the main lumen can be non-cylindrical in cross-section. In an alternative embodiment, the introducer sheath shaft is integrally coupled to the introducer sheath body.

Suture ring 45 is coupled to distal end 33 of sheath body 30. Suture ring 45 provides a mechanism allowing the practitioner to grasp introducer sheath 10 while also allowing introducer sheath 10 to be sutured or fastened to the patient when introducer sheath 10 has been properly placed. Suture ring 45 includes a proximal end 46 and an aperture 47. Proximal end 46 of suture ring 45 engages distal end 33 of introducer sheath body 30 to secure suture ring 45 to sheath body 30. Aperture 47 of suture ring 45 accommodates introducer sheath shaft 40. As will be appreciated by those skilled in the art, a variety of types and configurations of suture rings can be utilized without departing from the scope and spirit of the present invention. For example, in one embodiment the suture ring is rotatable about the axis of the introducer sheath shaft.

Figure 3:
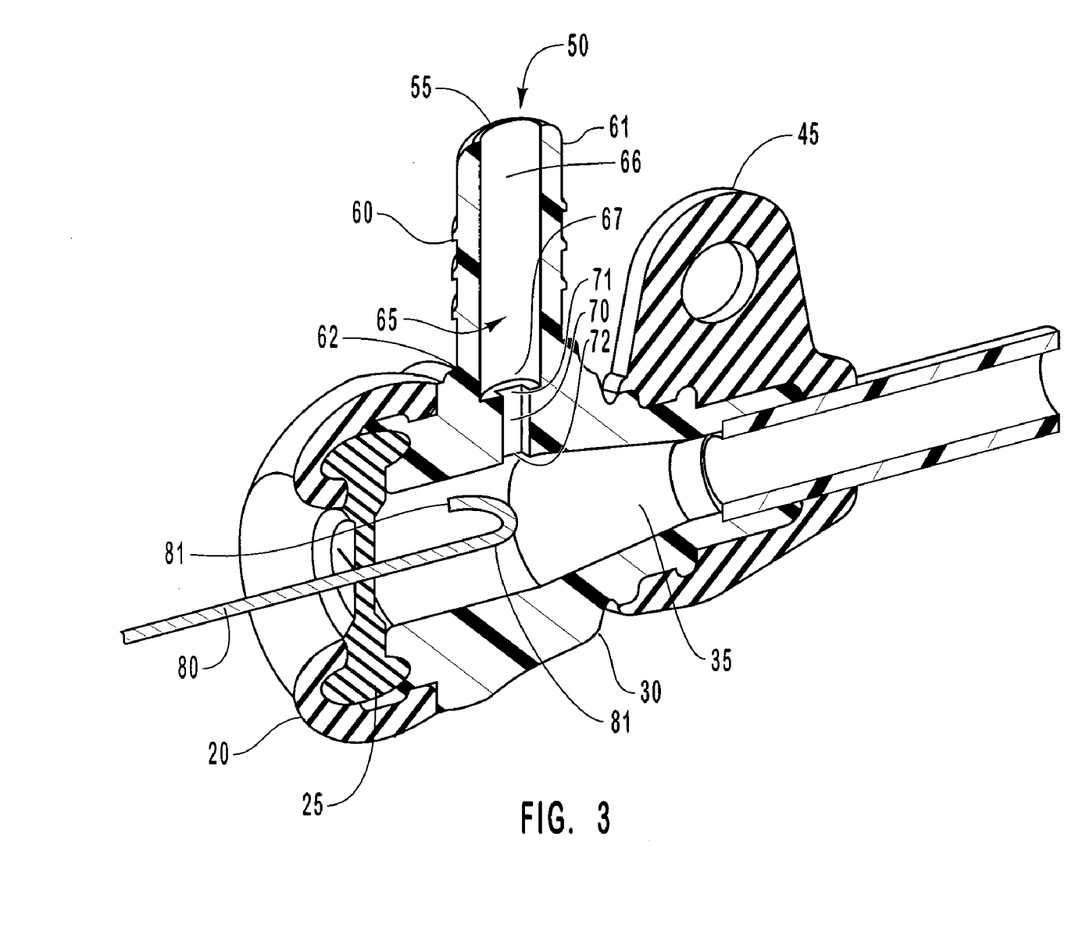
FIG. 3 is a cut-away view of the introducer sheath having a side port that is perpendicular to main lumen of the introducer sheath.

FIG. 3 is a cross-sectional view of introducer sheath 10 having a non-circular side port 50 positioned perpendicularly to introducer sheath 10. In the illustrated embodiment, the non-circular aspect of non-circular side port 50 comprises an internal bore 70 that is non-circular in configuration. In the illustrated embodiment, configuration of the non-circular side port 50 is configured to minimize inadvertent excursions of articles such as guide wire 80 from main lumen 35 into non-circular side port 50. Non-circular side port 50 includes an external aperture 55, a side port body 60, a side port lumen 65, and an internal bore 70. External aperture 55 of side port 50 is an opening defined by distal end 61 of side port body 60. External aperture 55 is in fluid communication with side port lumen 65 and allows for the introduction of guide wires, catheters, or other articles or materials to be introduced into side port lumen 65.

Side port body 60 provides support to other portions of side port 50. Side port body 60 houses side port lumen 65 and side port internal bore 70. Side port body 60 includes distal end 61 and proximal end 62. Distal end 61 of side port 60 defines external aperture 55 and is configured to accommodate a luer coupler, tubing, or other mechanisms of delivery for infusate, fluids, medicines, etc. As will be appreciated by those skilled in the art, a variety of types and configurations of attachment apparatuses can be utilized without departing from the scope and spirit of the present invention. For example in one embodiment, the distal end of the side port body can include an attachment apparatus that defines the external aperture. Such an apparatus can be integrally coupled with, threaded to, or otherwise connected to the distal end of the side port body.

Side port lumen 65 and side port internal bore 70 allow for the introduction of articles or materials into introducer sheath main lumen 35. Side port lumen 65 comprises a cavity within side port body 60 configured to receive saline, medicines, guide wires, catheters, or other materials. Such articles and materials pass from external aperture 55 through side port lumen 65 and internal bore 70 into introducer sheath main lumen 35. Side port lumen 65 includes distal end 66 and proximal end 67. Distal end 66 of side port lumen 65 is positioned adjacent side port external aperture 55. Proximal end 67 of side port lumen 65 is positioned adjacent to side port internal bore 70. Side port internal bore 70 comprises a space between side port lumen 65 and introducer sheath main lumen 35 in which guide wire, catheters or other materials can pass through before entering introducer sheath main lumen 35.

Side port internal bore 70 includes a distal end 71 and an internal end 72. Distal end 71 of side port internal bore 70 is in fluid connection with side port lumen 65 and internal end 72 of side port internal bore 70 is in fluid coupling with introducer sheath main lumen 35. As will be appreciated by those skilled in the art, a variety of types and configurations of the side port can be utilized without departing from the scope and spirit of the present invention. Thus, in some embodiments, the transverse diameter of the side port can vary from that of the illustrated embodiment.

In the illustrated embodiment, guide wire 80 is introduced through main lumen 35 of introducer sheath 10. Guide wire 80 is introduced from external opening 15 positioned in end cap 20 through seal 25 and into main lumen 35. Guide wire 80 includes a "j-type" distal end 81 comprising a curved tip, which is adapted to facilitate threading of guide wire 80 while preventing injury to the patient's blood vessel.

The "j-type" distal end 81 can interact with internal bore 70 of side port 50 as a user threads guide wire 80 through main lumen 35 of introducer sheath 10. In the illustrated embodiment, internal bore 70 has a non-circular cross-section. The non-circular cross-section has a minimum transverse dimension that is smaller than the diameter of guide wire 80. By utilizing a non-circular cross-section, the minimum transverse dimension of internal bore 70 can be prevent guide wire 80 from moving into side port 50 while allowing a greater amount of fluid flow. The greater amount of fluid flow is facilitated by providing a larger cross-sectional area than a circular side port having diameter smaller than the diameter of guide wire 80. The larger cross-sectional area allows a greater amount of fluid flow while being sufficiently narrow to stop movement of guide wire 80 into side port 50. The cross-sectional area of non-circular side port 50 will be discussed in greater detail in FIG. 4.

Figure 4:
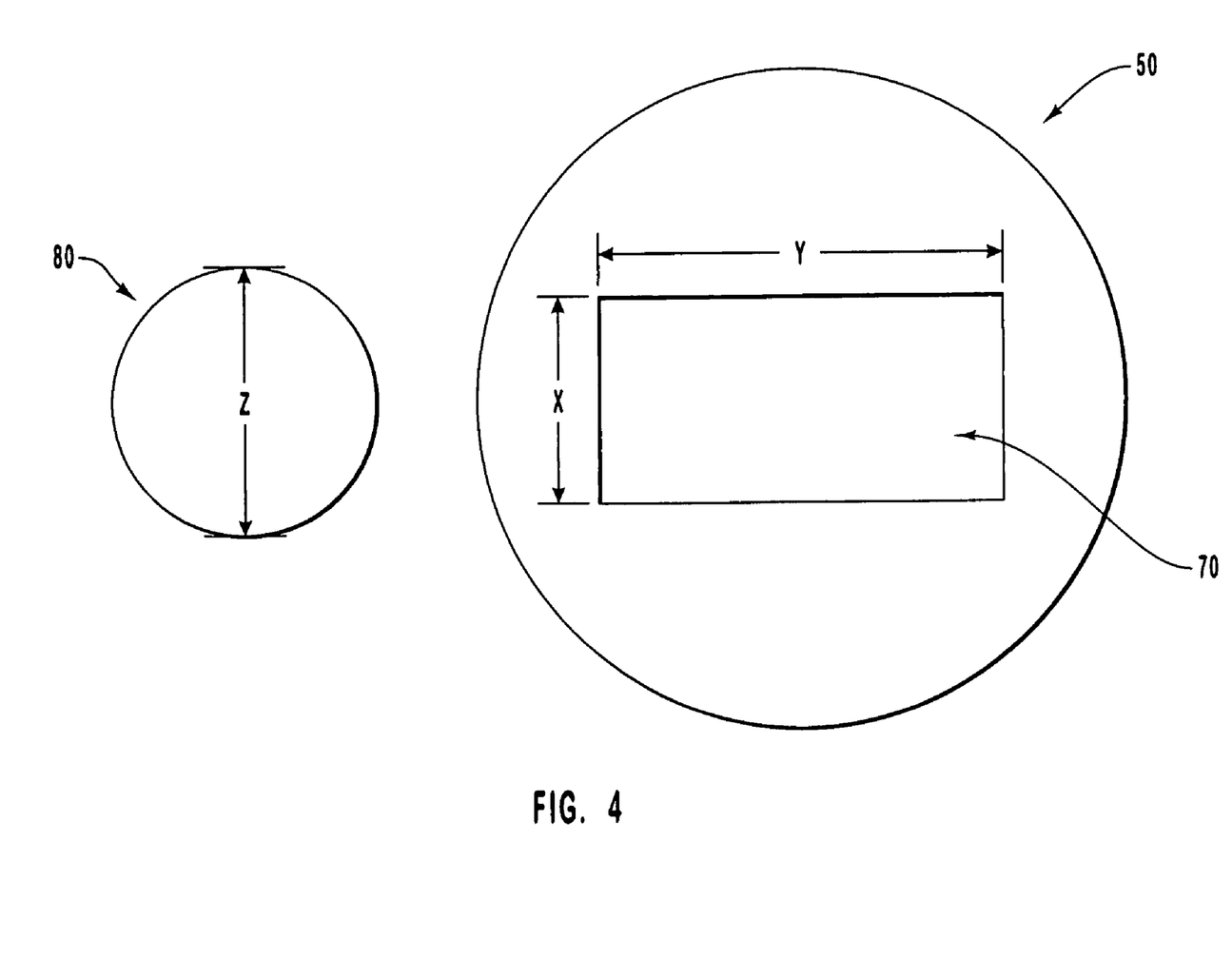
FIG. 4 is an illustrative cross section of an interior lumen of the side port illustrating the minimum transverse diameter of the side port lumen/internal bore relative to the diameter of a guide wire to be used with the introducer sheath.

FIG. 4 illustrates the non-circular cross section of internal bore 70 of sideport 50. In the illustrated embodiment, internal bore 70 of side port 50 includes an x-axis and a y-axis. Guide wire 80 has a diameter z. In the illustrated embodiment, the x-axis comprises the width of the cross-section of internal bore 70. The y-axis comprises the length of the cross-section of internal bore 70. The width of x-axis is smaller than the diameter z of guide wire 80. This prevents guide wire 80 from entering internal bore 70 of non-circular side port 50. In the illustrated embodiment, the x-axis comprises the minimum transverse dimension of the internal bore of the side port.

The total cross-sectional area of internal bore 70 is the product of the x-axis and the y-axis. The cross-sectional area of internal bore 70 is greater than a circular side port having diameter smaller than the diameter of guide wire 80. This is due to the fact that the length of the y-axis is sufficiently greater than diameter z of guide wire 80 so as to provide a greater overall cross sectional area. Thus, while the width of x-axis is smaller than diameter z of guide wire 80, the overall cross sectional area of internal bore 70 is larger than typical circular side ports due to the length of the y-axis of internal bore 70.

Figure 5:
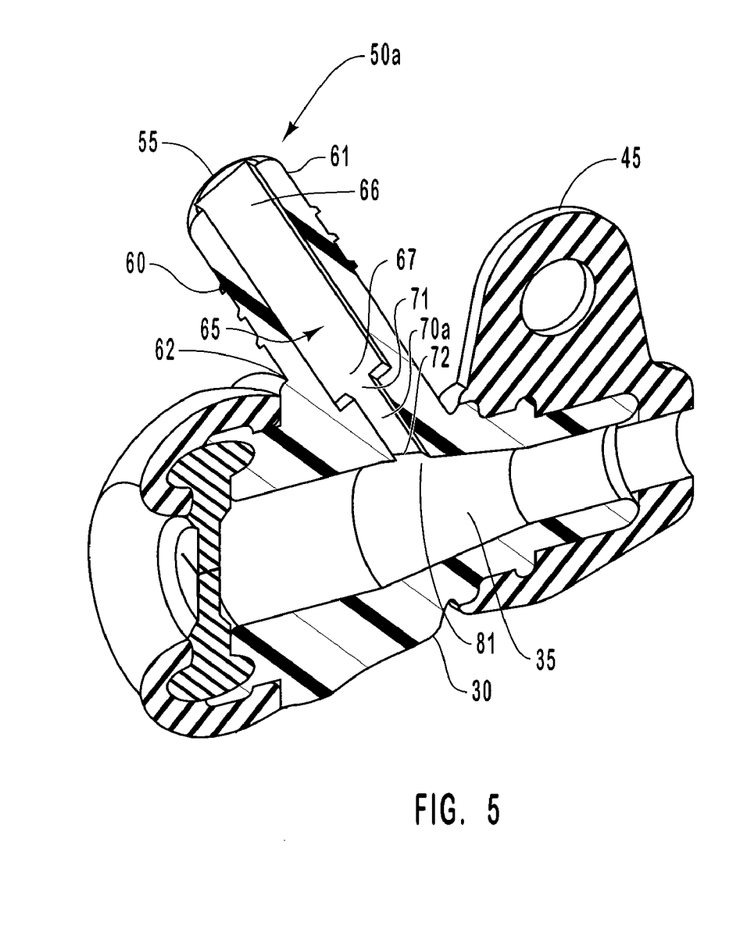
FIG. 5 is a cut-away perspective view of a non-circular side port that is non-perpendicular to the main lumen of the introducer sheath.

FIG. 5 illustrates a cross-sectional view of introducer sheath 10 having a non-circular side port 50a positioned non-perpendicularly to introducer sheath 10. Non-circular side port 50a is configured to minimize inadvertent excursions of articles such as guide wire 80 from main lumen 35 into non-circular side port 50a. Non-circular side port 50a includes external aperture 55, side port body 60, side port lumen 65, and internal bore 70a. External aperture 55 of side port 50 is an opening defined by distal end 61 of side port body 60. External aperture 55 is in fluid communication with side port lumen 65 and allows for the introduction of guide wires, catheters, or other articles or materials to be introduced into side port lumen 65.

The non-perpendicular configuration of non-circular side port 50a places internal bore 70a at an angle relative to main lumen 35 that further reduces the likelihood of excursion of the guide wire over the use of a non-circular cross section of the internal bore 70a alone. As will be appreciated by those skilled in the art, a variety of types and configurations of non-circular side ports can be utilized according to the present invention without departing from the scope and spirit of the present invention. In one embodiment, the non-circular cross section of the side port is provided by another portion of the side port than the internal bore. In another embodiment, the shape of the external aperture can vary from that of the illustrated embodiment. In one embodiment, the external aperture can be circular while in another embodiment, the shape can be non-circular. In another embodiment, the size of the external aperture relative to other components of the side port varies from that of the illustrated embodiment. For example, in one embodiment the size of the external aperture can be in the range of between 0.043-0.154 inches. In another embodiment, the width of the aperture is approximately 0.036 inches while the length of the aperture is approximately 0.080 inches. In another embodiment, the external aperture can have a transverse diameter similar to the side port lumen and/or internal bore. In yet another embodiment, the external aperture has a diameter that is larger or smaller than the side port lumen and/or internal bore.

Figure 6:
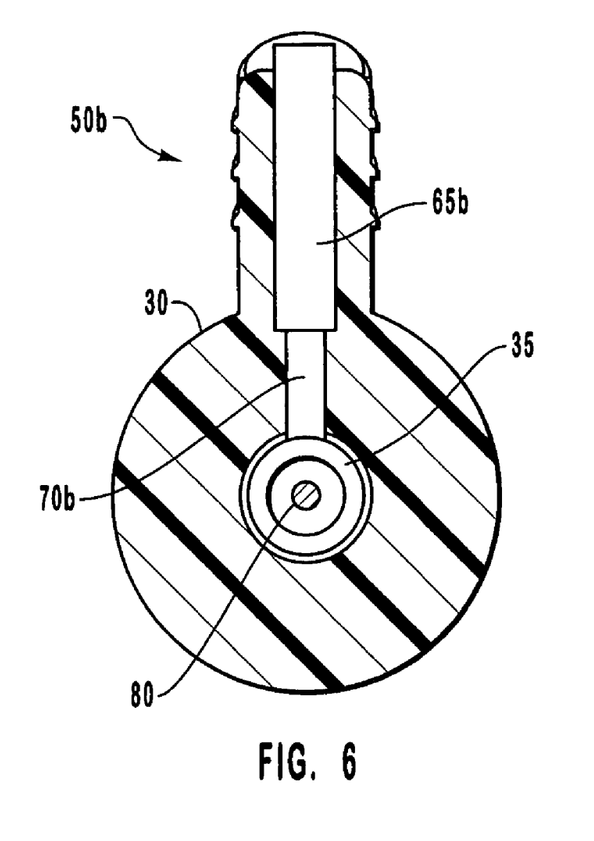
FIG. 6 illustrates a cut-away view of the side port having an internal bore located at the junction between the side port lumen and the introducer sheath main lumen such that the transverse diameter of the side port lumen is greater than the transverse diameter of the internal bore.

FIG. 6 illustrates a non-circular side port 50b having a side port lumen 65b of a transverse diameter that is greater than the transverse diameter of the internal bore 70b. In the illustrated embodiment, internal bore 70b is a lengthened structure wherein guide wires, catheters, or other articles or materials must pass through before entering the introducer sheath main lumen 35.

Figure 7:
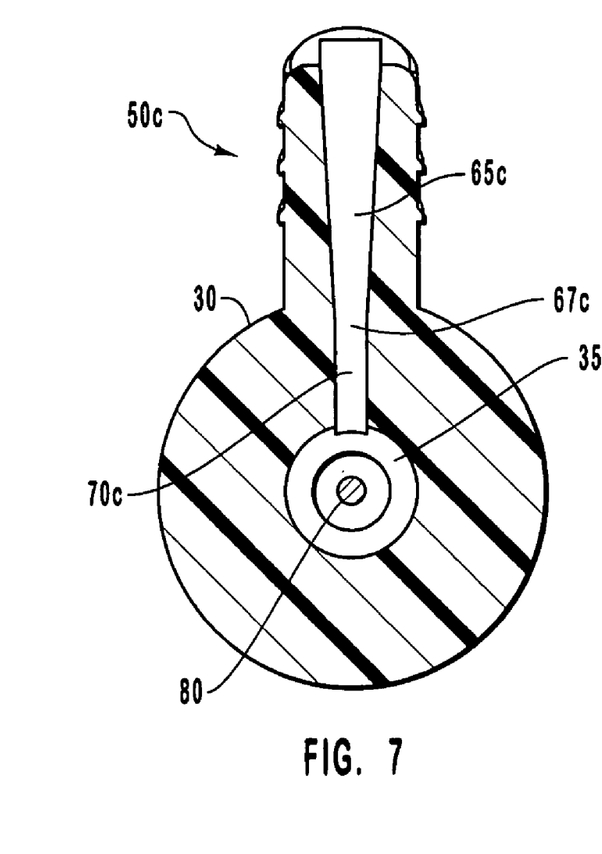
FIG. 7 illustrates a cut-away view of the side port having a side port lumen that tapers such that the transverse diameter of the lower tapered portion of the side port lumen is congruous with the transverse diameter of the internal bore.
Figure 8:
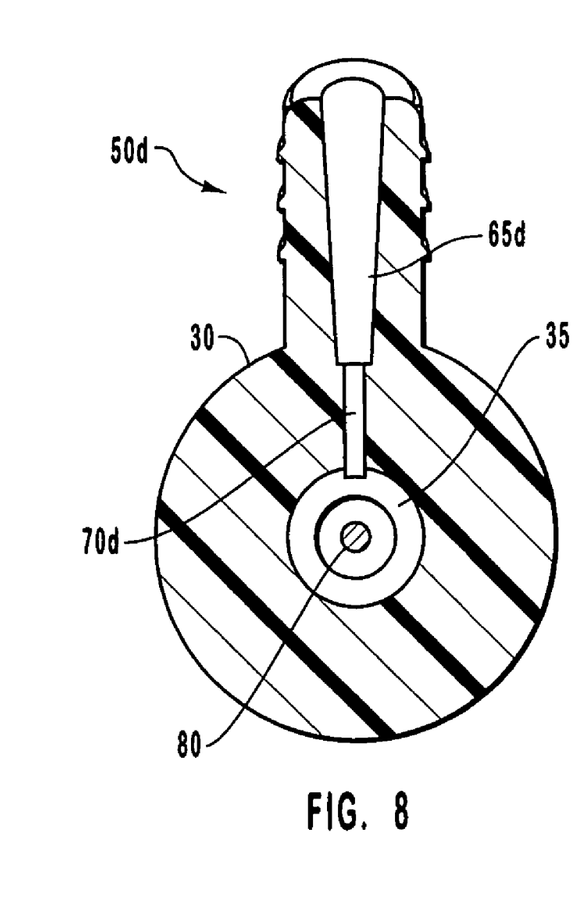
FIG. 8 illustrates a cutaway view of the side port having a side port lumen that tapers and the transverse direction of the side port lumen is greater than the transverse diameter of the internal bore.

FIGS. 7 and 8 illustrate non-circular side ports wherein the transverse diameter of the lower portion of the side port lumen is smaller than the transverse diameter of the external aperture due to tapered or other constricting configurations. FIG. 7 illustrates a non-circular side port 50c having a lower portion of the side port lumen 67c with a diameter similar to the transverse diameter of the internal bore 70c. The internal bore structure is lengthened while also being congruous with the side port lumen 35. The similarity in diameter is due to a "V" shape configuration of side port lumen 65c.

FIG. 8 illustrates an alternative embodiment wherein internal bore 70d is not congruous with a tapered side port lumen 65d. In the illustrated embodiment, the transverse diameter of side port lumen 65d is still greater than the transverse diameter of internal bore 70d despite tapering.

Figure 9:
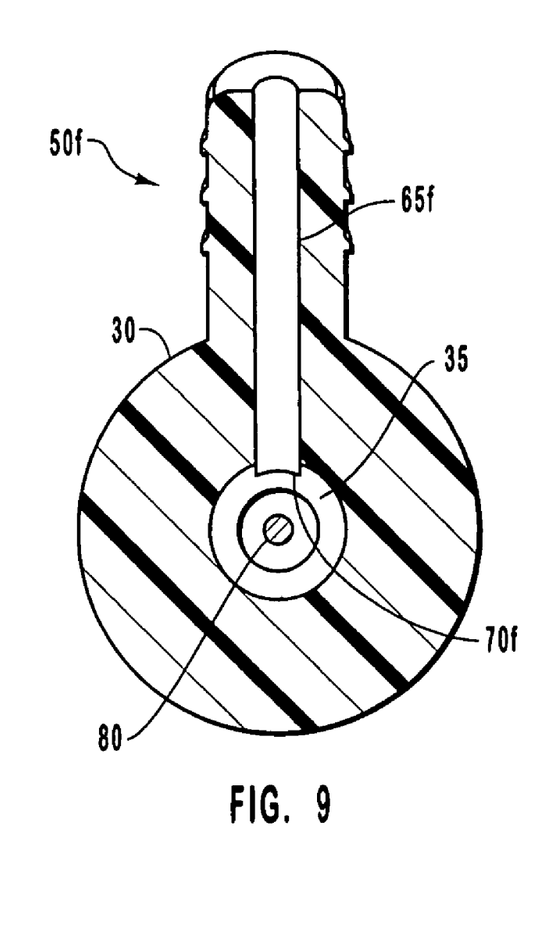
FIG. 9 illustrates a cutaway view of the side port having an internal bore of the same cross sectional area of the side port lumen.

FIG. 9 illustrates yet another alternative embodiment wherein the cross-section of the side port lumen 50f is the same as the cross section of the internal bore 70f. As will be appreciated by those skilled in the art, a variety of types and configurations of side ports can be utilized without departing from the scope and spirit of the present invention. For example, the side port lumen can be cylindrical, non-cylindrical, curved, or any other shape or configuration that allows the side port lumen to perform its intended functions.

FIG. 10A-10F illustrate a variety of shapes of a non-circular internal bores that can be utilized according to the present invention. The shapes and configurations of FIG. 10A-10F are depicted by way of an example and not a limitation. In the illustrated embodiment, the minimum transverse diameter of each of the illustrated non-circular side ports are about or less than 0.030 inches for a guide wire having a diameter of 0.038 inches. Nevertheless, the overall cross-sectional area of the internal bores of the non-circular sideports of FIG. 10A-10F are greater than the cross sectional area of circular sideports having diameters smaller than the diameter of guide wires to be utilized with the introducer sheath.

Figure 10A:
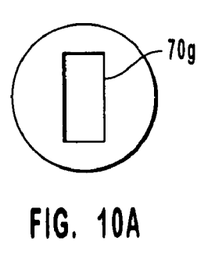
FIG. 10A-F illustrate variations of a transverse view of the internal bore of the side port.
Figure 10B:
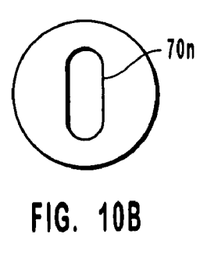
Figure 10C:
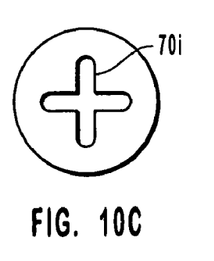
Figure 10D:
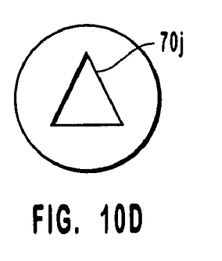
Figure 10E:
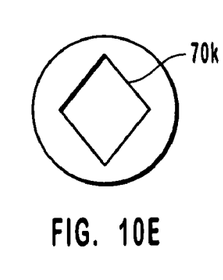
Figure 10F:
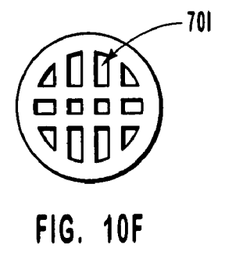

In FIG. 10A, the cross section of internal bore 70g is rectangular. In FIG. 10B, the cross section of the internal bore 70h is oval. In FIG. 10C, the cross section of internal bore 70i is cruciform. In FIG. 10D, the cross section of internal bore 70j is triangular. In FIG. 10E, the cross section of internal bore 70k is diamond shaped. In FIG. 10F, the cross section of the internal bore 70l comprises a plurality of intermittent apertures positioned in a screen-type fashion. In an alternative embodiment, the cross section of the internal bore is elliptical. In another embodiment, the cross section of the internal bore is substantially circular but includes a projection or separating member that prevents inadvertent excursion of a guide wire or other article or material.

Although the side port internal bore is the preferred noncircular component, any component of the side port as listed in the specification can qualify as a noncircular component. This invention also covers a side port with any combination of or all of the several components, as listed above, being noncircular and therefore able to prevent inadvertent excursions of a guide wire.

The present invention can be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An introducer sheath, the introducer sheath having a main lumen which is configured to allow the passage of a guidewire, medicine or other instruments or fluids into the vasculature of a patient while maintaining hemostasis at the vascular insertion site, the introducer sheath comprising:

an introducer sheath body comprising a hub of the introducer sheath, the introducer sheath body having a sidewall which defines a lumen of the introducer sheath body, the introducer sheath body adapted to be positioned external to the patient;

an introducer sheath shaft coupled to the introducer sheath body and extending distally from the introducer sheath hub, the introducer sheath shaft having a lumen which is in fluid communication with the lumen of the introducer sheath body, the introducer sheath shaft adapted to be advanced into the vasculature of the patient;

a seal adapted to be positioned within the introducer sheath body to maintain hemostasis of the introducer sheath body while allowing a guide wire or other medical instrument to be introduced through the lumen of the introducer sheath body into the lumen of the introducer sheath shaft and into the vasculature of the patient;

side port body linked to the sidewall of the introducer sheath hub, the side port body being in fluid communication with the main lumen of the introducer sheath hub wherein the side port body includes a non-circular internal bore positioned internal to the side port body and in communication with a lumen of the side port body, the internal bore operably coupled to the main lumen of the introducer sheath hub, wherein a cross-section of the non-circular internal bore has a minimum transverse dimension that is smaller than a diameter of an object to be introduced into the main lumen of the introducer sheath such that entry of the object into the non-circular internal bore is prevented and wherein an overall cross-sectional area of the cross-section of the non-circular internal bore is greater and allows a greater amount of fluid flow than a circular cross-sectional area having a diameter that is the same as the minimum transverse dimension of the non-circular internal bore.

2. The side port of claim 1, wherein the cross-section of the non-circular bore has a second transverse dimension that is greater than the minimum transverse dimension.

3. The side port of claim 1, wherein the cross section is rectangular.

4. The side port of claim 1, wherein the cross section is elliptical.

5. The side port of claim 1, wherein the cross section is oval.

6. The side port of claim 1, wherein the cross section is cruciform.

7. The side port of claim 1, wherein the cross section is triangular.

8. The side port of claim 1, wherein the cross section is diamond shaped.

9. The side port of claim 1, wherein the cross section comprises a plurality of intermittent apertures positioned in a screen-type fashioned.

10. The side port of claim 9, wherein the internal bore and the side port lumen have the same non-circular configuration.

11. The side port of claim 1, wherein the internal bore has a smaller transverse diameter than the side port lumen.

12. The side port of claim 11, wherein the minimum transverse dimension comprises the width of the non-circular internal bore.

13. The side port of claim 11, wherein the side port is positioned non-perpendicularly to the main lumen of the introducer sheath.

14. The side port of claim 11, wherein the non-circular internal bore has a larger cross-sectional area than a circular side port having the same minimum transverse diameter.

15. The side port of claim 14, wherein the larger cross sectional area allows a greater amount of fluid flow while being sufficiently narrow to stop movement of the guide wire into the side port.

16. The side port of claim 15, wherein the main lumen of the introducer sheath is adapted to accommodate a saline.

17. The side port of claim 15, wherein the main lumen of the introducer sheath is adapted to accommodate a combination of two or more of the following a guide wire, a catheter, a stent, saline, and medicines.

18. An introducer sheath, the introducer sheath having a main lumen which is configured to allow the passage of a guidewire, medicine or other instruments or fluids into the vasculature of a patient while maintaining hemostasis at the vascular insertion site, the introducer sheath comprising:

an introducer sheath body comprising an introducer sheath hub, the introducer sheath body having a sidewall which defines a lumen of the introducer sheath body, the introducer sheath body adapted to be positioned external to the patient;

an introducer sheath shaft coupled to the introducer sheath body and extending distally from the introducer sheath hub, the introducer sheath shaft having a lumen which is in fluid communication with the lumen of the introducer sheath body, the introducer sheath shaft adapted to be advanced into the vasculature of the patient;

a seal adapted to be positioned within the introducer sheath body to maintain hemostasis of the introducer sheath body while allowing guidewires and other medical instruments to be introduced through the lumen of the introducer sheath body into the lumen of the introducer sheath shaft and into the vasculature of the patient;

side port body linked to the sidewall of the introducer sheath body, the side port body being in fluid communication with the main lumen of the introducer sheath hub, wherein the side port body includes a side port lumen, an external aperture, and an internal bore, wherein at least one of the external aperture, side port lumen or internal bore are non-circular in cross-section such that the cross-section of the non-circular external aperture, side port lumen or internal bore has a minimum transverse dimension that is smaller than a diameter of an object to be introduced into the lumen of the introducer sheath hub such that entry of the object into the non-circular external aperture, side port lumen or internal bore is prevented and wherein an overall cross-sectional area of the cross-section of the non-circular aperture, side port or internal lumen bore is greater and allows a greater amount of fluid flow than a circular cross-sectional area having a diameter that is the same as the minimum transverse dimension of the non-circular external aperture, side port lumen or internal bore.

19. The side port of claim 18, wherein the object comprises a guide wire.

20. The side port of claim 19, wherein the non-circular component of the side port has a minimum transverse dimension that is equal to or less than 0.030 inches.

21. The side port of claim 18, wherein the guide wire includes a j-straightener on its proximal end.

22. An introducer sheath hub, the introducer sheath hub having a lumen for introducing a catheter, a guide wire, or infusate, and a side port providing a mechanism for introducing materials into the lumen of the introducer sheath hub, the side port comprising:

an introducer sheath body, the introducer sheath body having a sidewall which defines a lumen of the introducer sheath body, the introducer sheath body adapted to be positioned external to the patient and being adapted to be secured to a shaft of the introducer sheath, the introducer sheath being configured to extend distally and be advanced into the vasculature of the patient and adapted to receive a seal which is to be positioned within the introducer sheath body to maintain hemostasis of the introducer sheath body while allowing guidewires and other medical instruments to be introduced through the lumen of the introducer sheath body into the lumen of the introducer sheath shaft and into the vasculature of the patient;

a side port body operably coupled to the introducer sheath hub;

a side port lumen positioned internal to the side port body; and an external aperture permitting a user to introduce materials into the side port;

a non-circular internal bore linking the side port lumen with the lumen of the introducer sheath hub, the non-circular internal bore preventing passage of a guide wire from the lumen of the introducer sheath hub into the side port lumen utilizing a minimum transverse dimension that is smaller than a diameter of a guide wire to be introduced through the lumen of the introducer sheath hub wherein an overall cross-sectional area of a cross-section of the non-circular internal bore is greater and allows a greater amount of fluid flow than a circular cross-sectional area having a diameter that is the same as the minimum transverse dimension of the non-circular internal bore.

23. The side port of claim 22, wherein the side port is positioned perpendicularly to the lumen of the introducer sheath hub.

24. The side portion of claim 23, wherein the non-perpendicular positioning of the side port further reduces the likelihood of excursions of guide wires from the main lumen into the side port.

25. The side port of claim 24, wherein the larger cross sectional area allows a greater amount of fluid flow.

26. An introducer sheath, the introducer sheath having an introducer sheath hub, introducer sheath hub having a lumen for introducing a catheter, a guide wire, or infusate, and a side port providing a mechanism for introducing materials into the lumen of the introducer sheath hub, the side port comprising:

an introducer sheath body comprising a hub of the introducer sheath, the introducer sheath body having a sidewall which defines a lumen of the introducer sheath body, the introducer sheath body adapted to be positioned external to the patient and being adapted to be secured to a shaft of the introducer sheath which is adapted to extend distally and be advanced into the vasculature of the patient and adapted to receive a seal which is to be positioned within the introducer sheath body to maintain hemostasis of the introducer sheath body while allowing guidewires and other medical instruments to be introduced through the lumen of the introducer sheath body into the lumen of the introducer sheath shaft and into the vasculature of the patient;

a side port body linked to the introducer sheath body;

a side port lumen positioned internal to the side port body; and an external aperture permitting a user to introduce materials into the side port body;

a non-circular internal bore linking the side port lumen with the lumen of the introducer sheath, the cross-section of the non-circular bore having a minimum transverse dimension that is smaller than a diameter of an object to be introduced into the lumen of the introducer sheath such that entry of the object into the non-circular internal bore is prevented and wherein an overall cross-sectional area of the cross-section of the non-circular internal bore is greater and allows a greater amount of fluid flow than a circular cross-sectional area having a diameter that is the same as the minimum transverse dimension of the non-circular internal bore.

27. The side port of claim 26, wherein the main lumen of the introducer sheath is adapted to accommodate a guide wire.

28. The side port of claim 26, wherein the main lumen of the introducer sheath is adapted to accommodate a catheter.

29. The side port of claim 26, wherein the main lumen of the introducer sheath is adapted to accommodate a stent.

30. The side port of claim 26, wherein the main lumen of the introducer sheath is adapted to accommodate medicines.

* * * * *